(12) United States Patent
Becker et al.

(10) Patent No.: US 8,956,827 B2
(45) Date of Patent: Feb. 17, 2015

(54) HISTOLOGICAL METHOD

(75) Inventors: Klaus Becker, Vienna (AT); Hans-Ulrich Dodt, Vienna (AT); Nina Jährling, Vienna (AT)

(73) Assignee: Technische Universitat Wien, Vienna (AT)

( * ) Notice: Subject to any disclaimer, the term of this patent is extended or adjusted under 35 U.S.C. 154(b) by 236 days.

(21) Appl. No.: 13/637,916

(22) PCT Filed: Mar. 17, 2011

(86) PCT No.: PCT/EP2011/001315
§ 371 (c)(1),
(2), (4) Date: Sep. 27, 2012

(87) PCT Pub. No.: WO2011/124317
PCT Pub. Date: Oct. 13, 2011

(65) Prior Publication Data
US 2013/0023008 A1    Jan. 24, 2013

(30) Foreign Application Priority Data

Mar. 30, 2010 (DE) .......................... 10 2010 013 950

(51) Int. Cl.
G01N 1/30 (2006.01)
C12N 5/07 (2010.01)

(52) U.S. Cl.
CPC ........................................ *G01N 1/30* (2013.01)
USPC ........................................ 435/40.5; 435/325

(58) Field of Classification Search
None
See application file for complete search history.

(56) References Cited

U.S. PATENT DOCUMENTS

| 6,472,216 B1 | 10/2002 | Chiang | |
|---|---|---|---|
| 2003/0203000 A1* | 10/2003 | Schwarz et al. | 424/423 |
| 2004/0009098 A1 | 1/2004 | Torre-Bueno | |
| 2007/0105087 A1 | 5/2007 | Ban et al. | |
| 2007/0185346 A1* | 8/2007 | Vaidya | 562/401 |
| 2009/0098640 A1 | 4/2009 | Fischer | |

FOREIGN PATENT DOCUMENTS

| DE | 32 15 438 A1 | 11/1983 |
|---|---|---|
| WO | 00/20846 A1 | 4/2000 |
| WO | 2004/048970 A1 | 6/2004 |
| WO | 2008/104564 A1 | 9/2008 |

OTHER PUBLICATIONS

International Preliminary Report on Patentability, IB, Geneva, issued Oct. 2, 2012, incorporating the English Translation of the Written Opinion of the ISA, ISA/EP, Rijswijk, NL, mailed Jul. 18, 2011.
Hans-Ulrich Dodt et al: "Ultramicroscopy: three-dimensional visualization of neuronal networks in the whole mouse brain," Nature Methods, Vo. 4, No. 4, Apr. 2007, pp. 331-336.
Jahrling, N. et al.: "3D-Visualization of nerve fiber bundles by ultramicroscopy", Medical Laser Application, Elsevier, NL, vol. 23, No. 4, Nov. 1, 2008, pp. 209-215, XP025612475, ISSN: 1615-1615, DOI: DOI:10.1016/J.MLA.2008.06.001 [retrieved on Aug. 15, 2008] Histological processing on p. 210, Conclusion.
International Search Report and Written Opinion of the ISA for PCT/EP201 1/001315, ISA/EP, Rijswijk, NL, mailed Jul. 18, 2011.

* cited by examiner

*Primary Examiner* — Laura Schuberg
(74) *Attorney, Agent, or Firm* — Harness, Dickey & Pierce, P.L.C.

(57) ABSTRACT

The invention relates to the technical field of the histological preparation of biological tissue comprising a method and means for preparing transparent biological specimens for examination under a light microscope.

9 Claims, 2 Drawing Sheets

HISTOLOGICAL METHOD

CROSS-REFERENCE TO RELATED APPLICATIONS

Figure 1A:
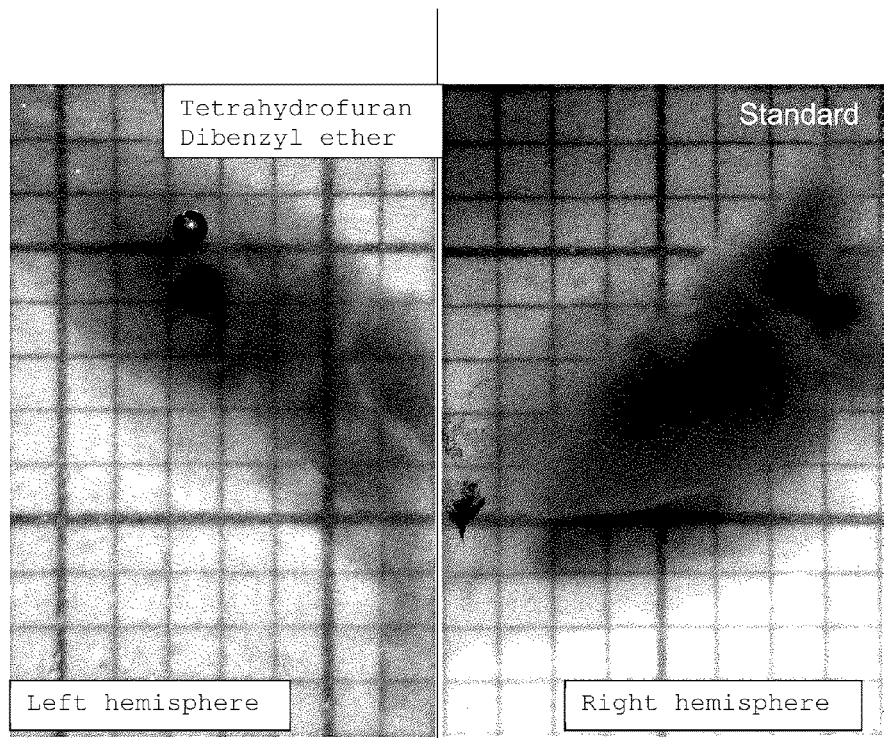

This application is a 371 U.S. National Stage of International Application No. PCT/EP2011/001315, filed Mar. 17, 2011, which claims priority to German Patent Application No. 10 2010 013 950.5, filed Mar. 30, 2010. The disclosures of the above applications are incorporated herein by reference.

The invention relates to the technical field of the histological preparation of biological tissue comprising a method and means for preparing transparent biological specimens for examination under a light microscope.

In the context of light microscopy, particularly fluorescence microscopy, of biological tissue specimens, particularly cells, it can be necessary to improve the transparency of the tissue for light, particularly for illumination and excitation light. Known measures, for the most part, reduce differences in the index of refraction within the tissue that cause undesired light scattering and prevent transparency. Any refraction of light at the transitions between media of different optical densities is to be suppressed. This process is referred to as "clearing." The prior art provides for the use of solvents, which have an optical index of refraction that is adjusted to the tissue structures, for the clearing action. These "clearing means" substitute the originally present optical media in the tissue with other indices of refraction, particularly intracellular and interstitial water and fat. A known clearing means composition is a mixture of benzyl alcohol and benzyl benzoate (BABB), commonly used at a ratio of 1:2.

For clearing purposes, the pre-fastened tissue is first dehydrated using an ascending sequence of drying means (dehydration agents). Known drying agents are organic polar solvents or solvent compositions such as, in particular, methanol, ethanol and octanol, if necessary, in connection with a solvent-mediating agent such as DMSO or a detergent. The dehydrated tissue is subsequently incubated in clearing agent that is to penetrate the tissue such that a cleared, meaning optically for the most part transparent, tissue specimen is obtained.

Effective tissue clearing is desired specifically in connection with light microscopy and, in particular, fluorescence microscopy examinations of neuronal tissue, specifically tissue specimens of the central nervous system. Neuronal tissue typically contains a high proportion of membrane-type, light-refracting structures. In view of the known clearing agents, there still remains potential for improvement of the obtained transparency in certain light microscopy techniques such as, in particular, the so called "light band microscopy" (ultramicroscopy); see, for example, Dodt et al., Nature Methods 4 (4): 331-336 (2007).

Using known clearing measures, to date it has only been possible to clear comparatively thin tissue sections; meaning, it has only been possible to achieve a transparency that allows for light microscopy, particularly fluorescence microscopy, examinations of such tissues. Light and fluorescence microscopy methods that require the presence of a transparent specimen can, disadvantageously, not be carried out on tissue samples or biopsates. It is desired to improve the clearing result in such a way that it is also possible, for the most part, to clear larger tissue sections as well such as, for example, tissue pieces of edge lengths of approximately 1 cm or more.

In tissue of genetically altered organisms, in which certain tissue cells express chromophoric marker proteins, said marker proteins are detectable under a light microscope. A known marker protein is "green fluorescent protein" (GFP), as well as variations of the same (xFP) including "enhanced green fluorescent protein" (EGFP). Other fluorescent marker proteins are "red fluorescent protein" of Discosoma sp. (dsRed) and variations thereof such as, for example, dsRed monomer or drFP583. Applying corresponding excitation light such as, for example, laser light (488 nm), this protein is excited to fluoresce. Fluorescence can also be registered by means of fluorescent-microscopic techniques such as, for example, ultramicroscopy, and the obtained image information can be evaluated thereafter. Other methods of fluorescence marking preferably utilize molecules that bind specifically to tissue structures such as, for example, antibodies that have fluorescent chromophores (dyes) coupled thereto. In addition, some tissues contain autofluorescent structures that demonstrate fluorescence, even without adding external chromophores or the expression of marker proteins.

There exists the problem that known measures for clearing tissue specimens, particularly the dehydration steps by means of known drying agents and clearance by means of known clearing agents, weaken the fluorescent signal and reversibly or irreversibly alter said signal. As a result, any fluorescence-microscopic examination of cleared tissue is rendered considerably more complicated or even impossible.

The technical task underlying the present invention consists in providing enhanced methods and means for preparing biological tissues allowing for improved clearance of the tissue in order to obtain better transparent tissue specimens. A further technical problem that is related to the former task is providing methods and means for preparing biological tissues that will not impair or prevent the fluorescence or staining of marker proteins or other chromophores in the tissue during preparation and that will not impair and/or prevent fluorescence or staining.

The technical problem is completely solved by providing a method for preparing biological tissue for light microscopy, particularly fluorescence microscopy and/or ultramicroscopy, wherein the method comprises at least the following steps that are implemented, in particular, in the order as shown below:

A tissue that is fastened in a step (a) is dehydrated in a subsequent step (b) using a drying agent. In a step (c) after that, the dehydrated tissue is cleared with a clearing agent. The method according to the invention is especially characterized in that a novel dehydration agent or a dehydration agent that is prepared in a novel manner is used in step (b).

The method according to the invention is especially also characterized in that a novel clearing agent and/or a clearing agent that is prepared in a novel manner is used in step (c). The clearing agent is selected from the group of aromatic ethers and compositions containing aromatic ethers having an optical index of refraction that is adjusted to the index of refraction of the tissue, in particular, corresponding to the same.

According to this first aspect, the invention thus provides for the use of a novel clearing agent, which is based on an aromatic ether. Surprisingly, it thus has been possible to achieve considerably improved transparency of the cleared tissue in contrast to the clearing results that are obtained with known clearing agents such as BABB. Moreover, surprisingly, this novel clearing agent allows for preserving any existing fluorescence or staining that is present inside the tissue, particularly the fluorescence of expressed marker proteins such as "green fluorescent protein" (GFP), "yellow fluorescent protein" (YFP), "red fluorescent protein" (RFP), "cyan fluorescent protein" (CFP), "blue fluorescent protein" (BFP) or any related proteins as well as other chromophores. In addition, autofluorescence often occurs in prepared tissue that can be, as envisioned by the invention, directly utilized for the microscopic examination. Surprisingly, the invention does not at all or only insignificantly suppress autofluorescence. This circumstance makes novel histological testing methods possible and allows for establishing better information regarding any examined tissue.

In a preferred embodied example, the clearing agent is an aromatic ether or a composition containing the same, and whereby said either or composition containing the same preferably has a dynamic viscosity at room temperature (21° C.) of less than Pa·s (6.000 cP). Preferably, the dynamic viscosity at room temperature is 5.4 Pa·s (5.400 cP) or less. Without wanting to rely on the theory, the comparatively low viscosity exhibited by the clearing agent according to the invention is favorable in furthering tissue penetration and promotes the clearing action even in thicker tissue layers that could not be sufficiently penetrated until now by the clearing agents as provided by the prior art.

A special embodiment according to the invention provides for the preparation of tissues from pathological tissue samples or biopsates that have been extracted from human or animal bodies. A typical application involves surgical material (resected material) extracted from a patient during surgery. The preparatory method advantageously also allows for extending the application of light band microscopy or ultramicroscopy to the field of pathological or diagnostic testing of tissue specimens or biopsies, specifically in tumor diagnostics. Advantageously, breast tissue or lung tissue or other tissue materials extracted from the body can now be tested for the presence of the cells of a carcinoma, etc. in a simplified and improved manner.

In a special embodiment, the aromatic ether that is used as clearing agent is free of aldehyde functions and hydroxy functions, as well as other reactive functions. Without wanting to rely on the theory, the presence of reactive groups, such as aldehyde functions and hydroxy functions in the clearing agent, suppress fluorescence or staining by chromophores, particularly that by marker proteins. Therefore, the invention preferably provides for avoiding any presence of such reactive groups in a clearing agent. A preferred aromatic ether is dibenzyl ether (CAS 103-50-4). One variant provides solely for the use of dibenzyl ether as clearing agent and no other solvent, particularly no further clearing agent.

The index of refraction of the clearing agent is preferably between 1.4 and 1.8, more preferred between 1.5 and 1.6. In a special embodiment of the invention, the index of refraction of the clearing agent and/or of the composition of the clearing agent is adjusted by adding at least one organic doping agent. The doping agent is preferably selected from the group consisting of organic molecules that are rich in electrons having, in particular, no fluorescence emission in the visible light range in order for them not to cover up or override the fluorescence signal of a chromophore or a marker protein. Preferably, doping agents are selected from triphenylmethane and benzoquinoline, as well as other corresponding organic, electron-rich molecules. The person skilled in the art is familiar with measures for adjusting the index of refraction by means of such doping agents.

According to a second aspect, or as a special embodiment of the previously mentioned first aspect, the invention provides in step (b) for the use of a drying agent based on tetrahydrofuran (THF, CAS 109-99-9) for dehydrating the tissue. Preferred as a dehydration agent is the exclusive use of tetrahydrofuran or of a solvent composition containing tetrahydrofuran. One variant envisions the exclusive use of tetrahydrofuran and of no further solvent, preferably no further substance.

The inventors surprisingly found that tetrahydrofuran allows for effectively dehydrating the tissue. Simultaneously, the fluorescence or staining by means of chromophores, particularly of marker proteins, is preserved and impaired to a significantly lesser degree than by known drying agents and methods as provided by the prior art.

Correspondingly, the object of the invention also includes the use of tetrahydrofuran as a drying agent in the fluorescence-preserving preparation of biological tissue, particularly in connection with the preparation for tissue clearing or resin embedding or other permanent preparation methods. Dehydration of the tissue with a drying agent is achieved, in particular, by the repeated incubation of the tissue in ascending solvent concentrations, specifically in a manner as known from the prior art.

Surprisingly, the inventors further found that in order to preserve the fluorescence or staining of marker proteins in the tissue, drying agents and/or clearing agents, preferably both, should be present in a form that is peroxide-free. As known from the prior art, organic solvents form reactive peroxides, particularly when they are in contact with atmospheric oxygen and/or subjected to high-energy (UV radiation). Therefore, the invention preferably provides that the drying agent and/or clearing agent, respectively, is free of peroxide, meaning that no peroxides are present whatsoever, at least at the time when preparation steps (b) and (c) are implemented. Freedom from peroxides means peroxide of an incidence of below 0.1% peroxide, preferably below 0.01%, especially preferred below 0.001% (volume content).

In a special embodiment of the invention, the absence of peroxides in these agents is achieved in that, preferably before implementing preparation steps (b) and (c), the same are removed from the drying and/or clearing agents by adsorption of any peroxide compounds, which may be present, to an inert carrier medium, particularly an activated, specifically, basic aluminum oxide, or related adsorption systems. The invention does not exclude other measures for removing peroxide compounds. A preferred embodiment provides for concentration by an adsorption chromatography means involving at least one chromatography column. Said process is implemented, if necessary, with pressure or vacuum support, in ways that are known in the art. Any obtained peroxide-free compounds or compositions are subsequently maintained or stored away from oxygen under an inert gas, particularly argon. Any new peroxide formation is prevented, if necessary, by adding stabilizing agents. Preferred stabilizing agents are BHT (3,5-di-tert-butyl-4-hydroxy toluene) and propyl gallate (propyl-3,4,5-trihydroxybenzoate); they are preferably used at concentrations of 100 to 400 ppm. Furthermore, the inventors surprisingly also found that such stabilizing agents also have a stabilizing effect on chromophores, such as marker proteins, thus supporting the preservation of fluorescence or staining.

A preferred embodied example envisions a fastening or pre-fastening of the tissue specimen in connection with or for the purpose of providing the tissue in step (a). This occurs, preferably, according to known methods by using one of the fastening means as provided by the prior art, preferably selected from among formalin, paraformaldehyde and substances and compositions of an analogous function thereto. A special embodiment envisions in situ pre-fastening of the tissue by means of perfusion. In a preferred variant, step (a) also includes removal of tissue from the donor organism and cutting the tissue to dimensions that are adjusted, respectively, to the requirements of the applied microscopic examinations and related issues.

A special embodiment of the method provides for an additional step (d) that is executed afterwards and in which the cleared tissue is embedded to create, preferably, a permanent specimen mount and/or for simplifying handling of the specimen during the microscopic examination. To this end, the invention preferably provides that the cleared tissue is embedded in step (d) in a synthetic resin composition, wherein the same also has an optical index of refraction that is adjusted to the index of refraction of the tissue in order to preserve transparency.

One preferred embodiment provides for adjusting the index of refraction of the synthetic resin composition by adding at least one of the previously described electron-rich doping agents such as, for example, triphenylmethane and benzoquinoline or others. Preferably, the index of refraction of the synthetic resin composition is 1.4 to 1.8, especially preferred 1.5 to 1.6, and particularly preferred 1.55.

The synthetic resin composition is an epoxy-based composition that contains at least one epoxy component, at least one hardener component and also, preferably, at least one additional softener component. The components are preferably blended at a volume ratio of approximately 55 to 65% resin to 40 to 30% hardener to 8 to 2% softener. Advantageously, the presence of the clearing agent provided according to the invention, which can also serve as a softener of the synthetic resin composition, allows for easier penetration of the tissue by the synthetic resin composition.

Another object of the invention is a kit (kit of parts) that is provided for the purpose of preparing biological tissue and expedient for use in the context of light microscopy, and that is in fact used for this purpose. According to the invention, the kit contains at least the preferred peroxide-free, aromatic ether or a composition containing the same having an optical index of refraction, which is adjusted to the index of refraction of the tissue, as a clearing agent. The aromatic ether dibenzyl ether is preferred. Preferably, the kit contains dibenzyl ether exclusively as a clearing agent. In a preferred embodiment, the kit also contains, preferably, peroxide-free tetrahydrofuran or a solvent composition containing the same as a drying agent. It is especially preferred for the kit to contain tetrahydrofuran exclusively as a drying agent.

In a further embodiment, the kit contains, in addition, a synthetic resin composition containing an epoxy resin component, a hardener component and a softener component, wherein the synthetic resin composition has a index of refraction that is adjusted to the index of refraction of the tissue.

Another object of the invention is the use of, preferably, peroxide-free, aromatic ether or a composition containing the same having an optical index of refraction, which is adjusted to the index of refraction of biological tissue, as a clearing agent for the purpose of preparing the tissue for examination under the light microscope.

A further object of the invention is the use of, preferably, peroxide-free, aromatic ether or of a composition containing the same having an optical index of refraction, which is adjusted to the index of refraction of biological tissue, as a clearing agent for the purpose of preserving fluorescence marking of tissue for the preparation of the same for examination under the light microscope.

A preferred embodiment provides for mediation of the fluorescence marking of the tissue by the expression of one or multiple fluorescent or chromophorous proteins. In a preferred variant, the same are selected from a "green fluorescent protein" (GFP) and xFP variations thereof and "enhanced green fluorescent protein" (EGFP) as well as analogous chromophorous marker proteins. Other preferred fluorescent proteins are "red fluorescent protein" RFP, such as dsRed and variations thereof such as drFP583, as well as chromophorous marker proteins that are analogous thereto. Other preferred fluorescent proteins are "yellow fluorescent protein"YFP and variations thereof as well as any analogous chromophorous marker proteins. Other preferred fluorescent proteins are "cyan fluorescent protein" CFP and variations thereof as well as any analogous chromophorous marker proteins. Other preferred fluorescent proteins are "blue fluorescent protein" BFP and variations thereof as well as any analogous chromophorous marker proteins. The invention, however, is not limited to these aforementioned examples of autofluorescent proteins, which are quite concrete.

Furthermore, the fluorescence marking of the tissue can be based, additionally or alternatively, exclusively on fluorescence originating from autofluorescent structures contained in the tissue.

In addition, the fluorescence marking of the tissue can, additionally or alternatively, be based exclusively on other fluorescence markings of tissues as known from the prior art. At least one specific marking agent having a fluorescent chromophore coupled thereto is preferred, wherein the marking agent is selected from among monoclonal antibodies, polyclonal antibodies and other molecules that specifically bind to tissue structures. These include, for example, tumor-specific stains.

Correspondingly, the use of, preferably, peroxide-free aromatic ether or of a composition containing the same having an optical index of refraction, which is adjusted to the index of refraction of the biological tissue, is an object of the present invention as a clearing means for the purpose of obtaining better transparency upon clearing the tissue, when it undergoes preparation for examination under a light microscope.

A preferred embodiment of the present invention provides that the tissue is a tissue specimen extracted from the human or animal body, preferably selected from surgical material (resected material) and biopsates. A particular embodiment for use is in the field of tumor diagnostics.

Finally, a further object of the present invention is a specimen, particularly a microscopic specimen, of a biological tissue that can be prepared or that is prepared using concretely the previously characterized clearing agent and/or drying agent, particularly according to the presently characterized method according to the invention for the preparation of biological tissue.

A special embodiment of the preparation according to the invention is a tissue specimen extracted from a human or animal body, preferably selected from surgical material (resected material) and biopsates, in particular, for purposes of pathological or diagnostic testing such as, for example, tumor diagnostics.

The invention will be illustrated in further detail based on the examples and figures below, while said examples and figures shall not limit the scope of the invention.

The figures show as follows:

FIG. 1A is a comparison representation of the results from the preparation of tissue from the same specimen (left and right hemispheres of a mouse brain). The right hemisphere (right half of the image) was cleared using a method known from the prior art (drying agent: ethanol; clearing agent: benzyl alcohol/benzyl benzoate (BABB)). The left hemisphere (left half of the image) was prepared according to an embodiment of the present invention (drying agent: tetrahydrofuran, clearing agent: dibenzyl ether). Based on the improved visibility of the pattern of the underlying plotting paper, the enhanced transparency of the hemisphere that was prepared according to the invention is immediately discernable.

Figure 1B:
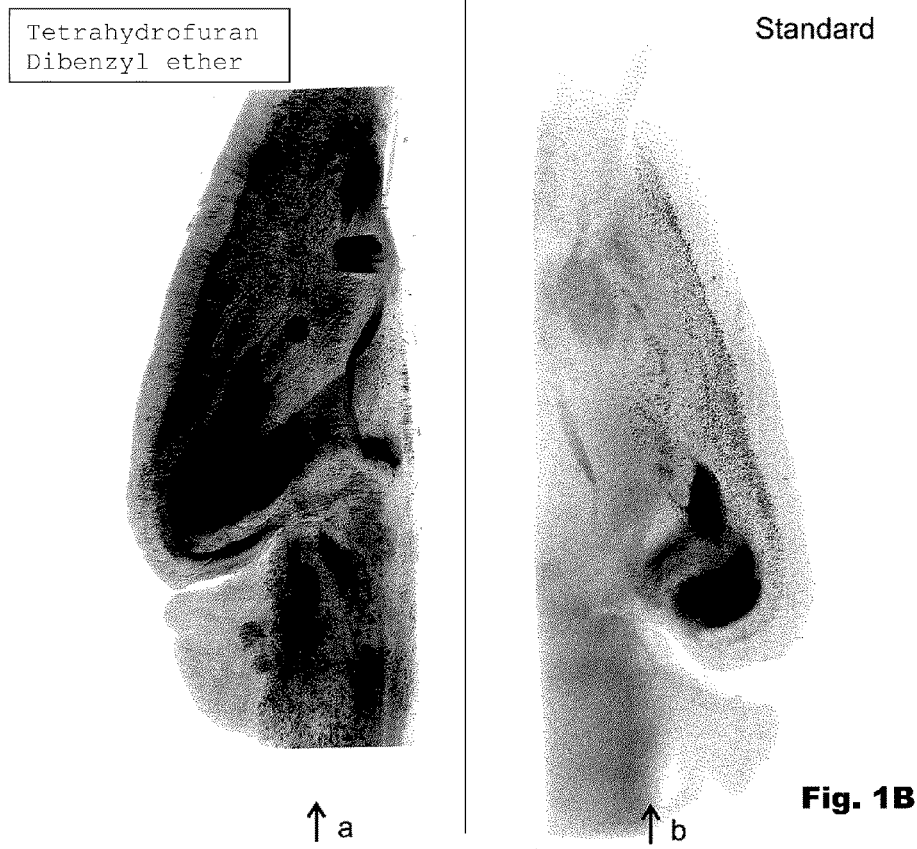

FIG. 1B shows the results of a fluorescence-microscopic examination by means of light band microscopy (ultramicroscopy) of the prepared pieces of tissue as represented in FIG. 1A (according to the invention: left; comparison example: right). The fluorescent marker protein GFP was expressed in both specimen halves. The inverted representation that has been chosen in the present instance, shows the fluorescence as blackening. Visibly stronger fluorescence can be seen in the sample prepared according to the invention (left half of the image).

Figure 2:
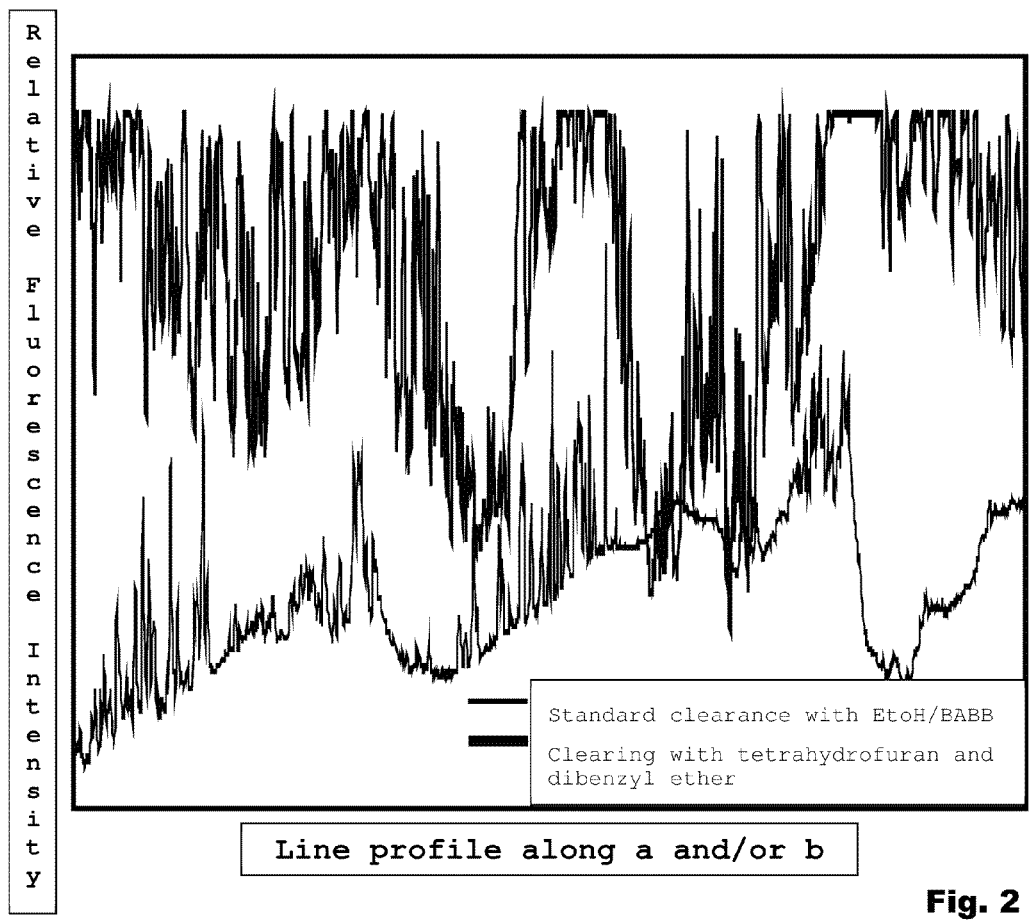

FIG. 2 shows a quantitative comparison of the intensity of the fluorescence signal along two same-location profiles through the specimens according to FIG. 1B. The profile lines are marked in FIG. 1B by the arrows a and b. The tissue that has been prepared according to the invention shows significantly higher fluorescence intensity (upper curve).

EXAMPLE

Preparation of CNS Tissue for Ultramicroscopy

Tissue slices are prepared of the brains of transgenic mice that express the fluorescent marker protein GFP in a subgroup of neurons, and they are examined ultramicroscopically. To this end, following anesthesia, the mice are subjected for ten minutes to a transcardial perfusion with 50 ml ice-cooled 0.1 mmol/l PBS (pH 7.6) with 1,000 U/ml heparin, respectively. Then follows the pre-fastening of the tissue by a 20-minute perfusion with 100 ml 4% paraformaldehyde in 0.1 mmol/l ice-cooled PBS, respectively. Transsection over the course of approximately five minutes ends with the removal of the brain. The brain is incubated for approximately twelve hours in 15 ml 4% paraformaldehyde in 0.1 mmol/l PBS at 4° C. Then the fastening agent is washed out for one hour by incubation in fresh 0.1 mmol/l PBS. The washing process is repeated three times.

The water removal according to the invention (dehydration) is achieved by incubation over twelve hours, respectively, with an ascending concentration series of peroxide-free tetrahydrofuran: 1st 50 vol %; 2nd 80 vol %; 3rd 96 vol %; 4th and 5th 100 vol % (5×12 hours). Then follows clearing by triple incubation for twelve hours, respectively, in peroxide-free dibenzyl ether.

The absence of peroxide in the drying and clearing agents is achieved in an earlier step by means of a separation of the peroxide using column chromatography on activated basic AlOx (according to Brockmann, activity 1). Due to the higher viscosity of dibenzyl ether, separation therein occurs by vacuum filtration. The obtained peroxide-free solvents are stored away from oxygen (inert gas: argon). BHT can be used as a stabilizer.

The obtained tissue specimen is transparent and immediately usable in ultramicroscopy (FIGS. 1 and 2). Optionally, the cleared tissue specimen can be embedded in a synthetic resin composition for a permanent mount of the specimen. A mixture consisting of the synthetic resin "E12," hardener "E1" and softener "AE10" (by the company Biodur of Heidelberg, respectively) at a volume ratio of 60:35:5 is used to this end, having a index of refraction that was adjusted with triphenylmethane. The cleared specimen is incubated therein. At approximately 50° C., the mixture hardens into completely transparent blocks having an index of refraction of approximately 1.55. GFP fluorescence remains intact for the most part, even after the specimen has been embedded.

The invention claimed is:

1. A method for preparing biological tissues in order to clear the tissue for light microscopy, the method comprising:
   a) fastening the tissue;
   b) dehydrating the tissue using a drying agent; and
   c) clearing the dehydrated tissue using dibenzyl ether or a composition containing dibenzyl ether having an optical index of refraction, which is adjusted to an index of refraction of the tissue, as a clearing agent.

2. The method according to claim 1, wherein the drying agent is tetrahydrofuran (THF) or a solvent composition containing THF.

3. The method according to claim 1, wherein the drying agent and the clearing agent are free of any peroxides at the time of the implementation of steps b) and c), respectively.

4. The method according to claim 1, wherein the drying agent and the clearing agent are freed of peroxide by adsorption to an inert carrier medium before steps b) and c) are implemented, respectively, and then maintained under an inert gas.

5. The method according to claim 4, wherein the drying agent and the clearing agent are each freed of peroxide by adsorption to activated basic aluminum oxide.

6. The method according to claim 1, wherein the fastening of the tissue is carried out with a fastening means that is selected from among formalin, paraformaldehyde and functionally analogous substances and compositions.

7. The method according to claim 1, wherein the index or refraction of the clearing agent is adjusted by adding at least one organic doping agent to the clearing agent.

8. The method according to claim 7, wherein the at least one organic doping agent is selected from the group consisting of triphenylmethane and benzoquinoline, and other organic, electron-rich molecules that do not exhibit any fluorescence emission in the visible light spectrum.

9. The method according to claim 1, further including:
   d) embedding the cleared tissue in a synthetic resin composition containing an epoxy resin component, hardener component and softener component, wherein the synthetic resin composition has an optical index of refraction that is adjusted to the index of refraction of the tissue.

* * * * *